(12) United States Patent
Bhat et al.

(10) Patent No.: US 10,329,249 B1
(45) Date of Patent: Jun. 25, 2019

(54) SULINDAC DERIVATIVES

(71) Applicant: KING SAUD UNIVERSITY, Riyadh (SA)

(72) Inventors: Mashooq Ahmad Bhat, Riyadh (SA); Mohamed A. Al-Omar, Riyadh (SA); Nawaf Abdulaziz Alsaif, Riyadh (SA); Syed Hidayathulla, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/151,291

(22) Filed: Oct. 3, 2018

(51) Int. Cl.
*C07C 325/02* (2006.01)
*A61P 29/00* (2006.01)

(52) U.S. Cl.
CPC ............ *C07C 325/02* (2013.01); *A61P 29/00* (2018.01); *C07C 2602/08* (2017.05)

(58) Field of Classification Search
CPC ............................... C07C 325/02; A61P 29/00
See application file for complete search history.

(56) References Cited

U.S. PATENT DOCUMENTS

| | | | |
|---|---|---|---|
| 8,044,048 B2 | 10/2011 | Piazza et al. | |
| 8,569,335 B2 | 10/2013 | Vizioli et al. | |
| 9,808,443 B1 | 11/2017 | Bhat et al. | |
| 2005/0250839 A1 | 11/2005 | Marnett et al. | |
| 2008/0207751 A1* | 8/2008 | Sparatore ............... | C07C 381/04 514/532 |

OTHER PUBLICATIONS

Azizian et al., "Arylhydrazone derivatives of naproxen as new analgesic and anti-inflammatory agents: Design, synthesis and molecular docking studies," Journal of Molecular Graphics and Modelling, 67, 2016, pp. 127-136.

Fogli et al., "Therapeutic potential of sulindac hydroxamic acid against human pancreatic and colonic cancer cells," European Journal of Medicinal Chemistry, 45, 2010, pp. 5100-5107.

Baldwin and Rorison, "Structural requirements for the binding of non-steroidal anti-inflammatory drugs to the 78 -Da gastrin binding protein," Biochimica et Biophysica Acta, 1428, 1999, pp. 68-76.

Chennamaneni et al., "COX inhibitors Indomethacin and Sulindac derivatives as antiproliferative agents: Synthesis, biological evaluation, and mechanism investigation," European Journal of Medicinal Chemistry, 56, 2012, pp. 17-29.

Bhat et al., "Design and Synthesis of N-Arylphthalimides as Inhibitors of Glucocorticoid-Induced TNF Receptor-Related Protein, Proinflammatory Mediators, and Cytokines in Carrageenan-Induced Lung Inflammation," Journal of Medicinal Chemistry, 58, 2015, pp. 8850-8867.

* cited by examiner

*Primary Examiner* — Rebecca L Anderson
(74) *Attorney, Agent, or Firm* — Richard C. Litman

(57) ABSTRACT

The sulindac derivatives are compounds of the formula:

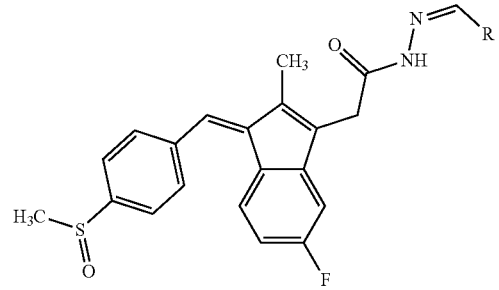

wherein R is one of twenty-five substituted or unsubstituted phenyl substituents; and pharmaceutically acceptable salts thereof. The sulindac derivatives are synthesized by refluxing sulindac hydrazide with appropriately substituted benzaldehydes in the presence of ethanol and catalytic amounts of glacial acetic acid. The sulindac derivatives may be used as active ingredients in pharmaceutical compositions for the treatment of inflammation or inflammatory diseases. The sulindac derivatives may also be used as analgesic and/or gastric sparing agents.

7 Claims, 2 Drawing Sheets

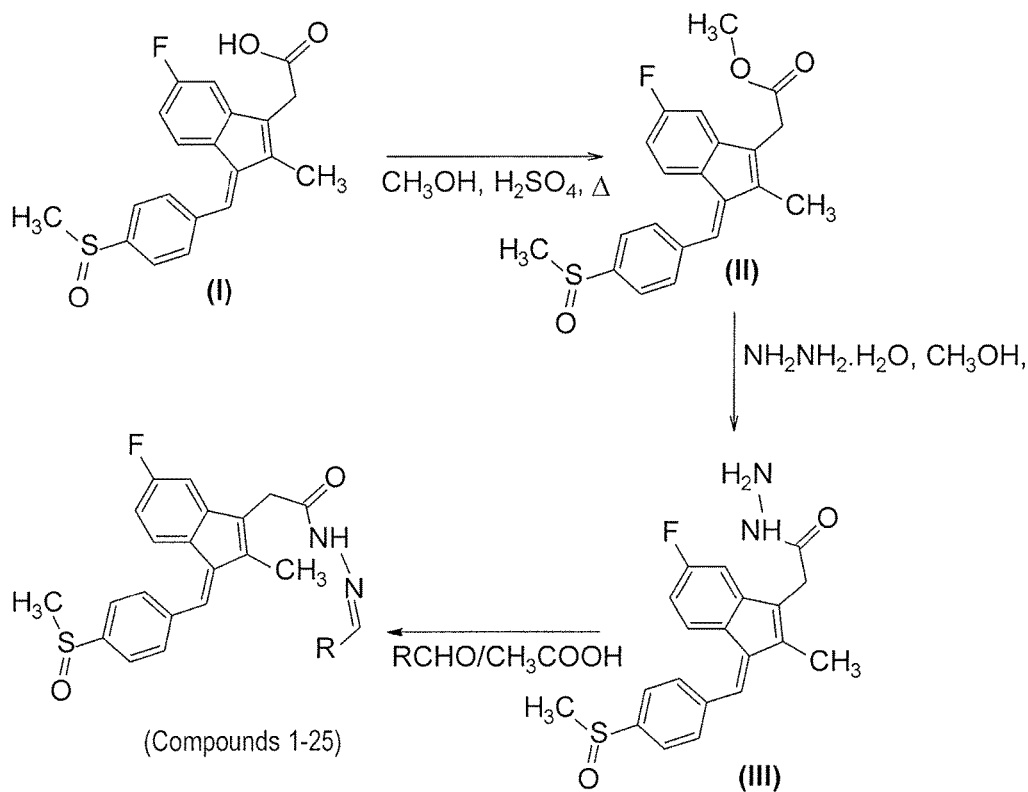

| Compound | R | Compound | R |
|---|---|---|---|
| 1 | 2-Nitrophenyl | 14 | 2,3-Dimethoxyphenyl |
| 2 | 4- Nitrophenyl | 15 | 3,4-Dimethoxyphenyl |
| 3 | Phenyl | 16 | 2,4,6-Trimethoxyphenyl |
| 4 | 4-Chlorophenyl | 17 | 2,3,4-Trimethoxyphenyl |
| 5 | 3-Hydroxyphenyl | 18 | 3-Methoxy-4-ethoxyphenyl |
| 6 | 3-Methoxyphenyl | 19 | 4-Hydroxy-3,5-dimethoxyphenyl |
| 7 | 3-Nitrophenyl | 20 | 4-Hydroxy-3-ethoxyphenyl |
| 8 | 4-Dimethylaminophenyl | 21 | 2,5-Dihydroxyphenyl |
| 9 | 2,4,5-Trimethoxyphenyl | 22 | 3-Hydroxy-4-methoxyphenyl |
| 10 | 3,4,5-Trimethoxyphenyl | 23 | 2,3-Dihydroxyphenyl |
| 11 | 4- Hydroxyphenyl | 24 | 2-Hydroxy-3-methoxy |
| 12 | 2-Methoxyphenyl | 25 | 2,3,4-Trihydroxyphenyl |
| 13 | 2,4-Dimethoxyphenyl | | |

*FIG. 2*

SULINDAC DERIVATIVES

BACKGROUND

1. Field

The disclosure of the present patent application relates to pharmaceutical compositions, and particularly to sulindac derivatives.

2. Description of the Related Art

Conversion of arachidonic acid to prostaglandin 1-12 (PGH2) is catalyzed by the cyclooxygenase (COX) enzyme. Because the prostaglandin H2 is an unstable intermediate, it is converted to many prostanoids by specific isomerase enzymes. This process of biosynthesis occurs in all tissues of the human body. Pain and fever associated with inflammation are the non-beneficial effects of prostaglandins, while gastrointestinal protection and platelet function are among their beneficial effects. The COX enzyme has two isoforms, COX-1 and COX-2, which are each regulated differently. COX-1 provides cytoprotection in the gastrointestinal (GI) tract, and COX-2 mediates inflammation.

Non-steroidal anti-inflammatory drugs (NSAIDs) are effective analgesics frequently used in palliative care. These medicines often demonstrate adverse side effects that are largely due to gastrointestinal toxicity, as well as subsequent complications, such as gastro-duodenal perforations, ulcers and bleeding. NSAID toxicity is typically ascribed to the inhibition of cyclooxygenase-1 (COX-1). Thus, selective inhibitors of cyclooxygenase-2 (COX-2) were developed in an attempt to reduce these side effects. Trial studies to date confirm that these drugs do indeed have a reduced incidence of gastro-duodenal toxicity. Prior to the introduction of the COX-2 selective inhibitors, patients at high risk were often prescribed a gastro-protective agent (such as misoprostol or a proton pump inhibitor) with a conventional NSAID.

Most of the common non-steroidal anti-inflammatory drugs (NSAIDs) show a greater selectivity for COX-1 than COX-2. Thus, long term use of NSAIDS may produce gastric irritation, bleeding and ulceration. It is assumed that inhibition of COX-2 selectively would result in the same anti-inflammatory benefits that non-selective NSAIDs provide, but with fewer incidences of gastrointestinal side effects. COX-2 inhibitors provide synthesis of cytoprotection prostaglandins, reducing ulceration and bleeding. However, some COX-2 inhibitors have also been found to have cardiovascular side effects.

Sulindac is an indene derivative NSAID known to induce ulceration. Chemical modifications have improved the safety profile of various NSAIDs, thus showing the possibility for synthetic modifications to result in an increased anti-inflammatory activity with reduced ulcerogenicity. It would be desirable to provide an indene derivative having the anti-inflammatory and analgesic properties of a COX-2 inhibitor NSAID, but which also provides gastric sparing activity.

Thus, sulindac derivatives solving the aforementioned problems are desired.

SUMMARY

The sulindac derivatives are compounds of the formula:

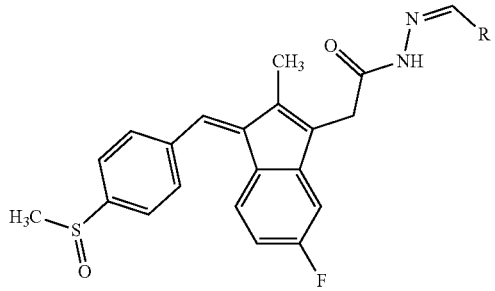

wherein R is selected from the group consisting of 2-nitrophenyl; 4-nitrophenyl; phenyl; 4-chlorophenyl; 3-hydroxyphenyl; 3-methoxyphenyl; 3-nitrophenyl; 4-dimethylaminophenyl; 2,4,5-trimethoxyphenyl; 3,4,5-trimethoxyphenyl; 4-hydroxyphenyl; 2-methoxyphenyl; 2,4-dimethoxyphenyl; 2,3-dimethoxyphenyl; 3,4-dimethoxyphenyl; 2,4,6-trimethoxyphenyl; 2,3,4-trimethoxyphenyl; 3-methoxy-4-ethoxyphenyl; 3,5-dimethoxy-4-hydroxyphenyl; 3-ethoxy-4-hydroxyphenyl; 2,5-dihydroxyphenyl; 3-hydroxy-4-methoxyphenyl; 2,3-dihydroxyphenyl; 2-hydroxy-3-methoxyphenyl; and 2,3,4-trihydroxyphenyl; and pharmaceutically acceptable salts thereof.

The sulindac derivatives may be used as an active ingredient of a pharmaceutical for use in treating inflammation or inflammatory diseases.

The sulindac derivatives may be used as analgesic and/or gastric sparing agents.

These and other features of the present invention will become readily apparent upon further review of the following specification and drawing.

BRIEF DESCRIPTION OF THE DRAWINGS

FIG. 2 is a reaction scheme for synthesizing sulindac derivatives.

Similar reference characters denote corresponding features consistently throughout the attached drawings.

DETAILED DESCRIPTION OF THE PREFERRED EMBODIMENTS

Figure 1:
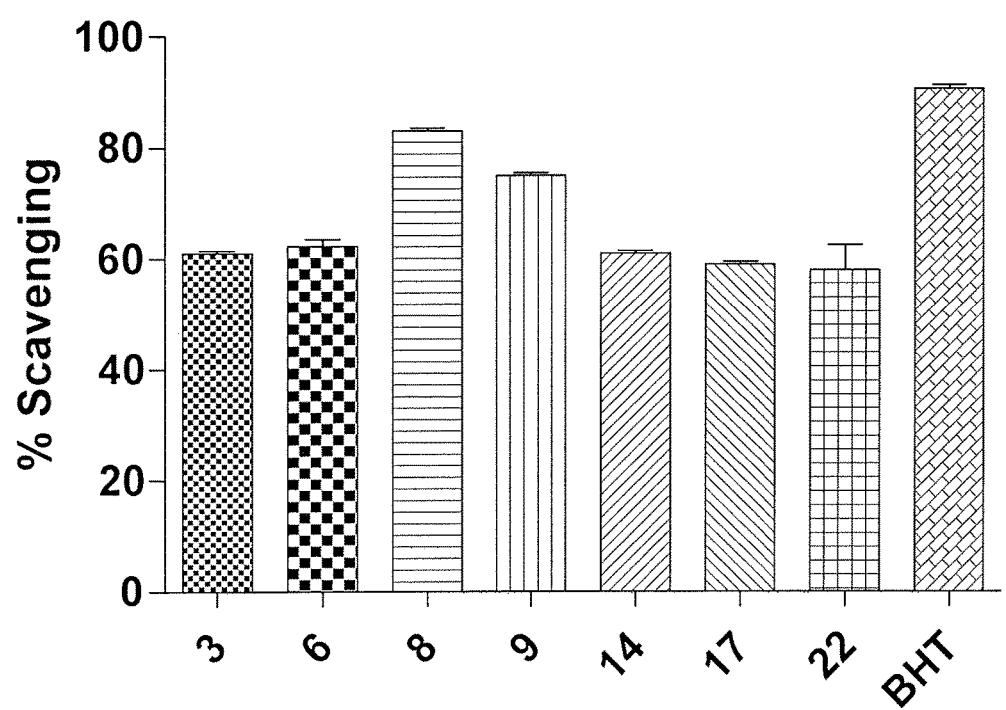
FIG. 1 is a plot of DPPH scavenging activity of the sulindac derivatives described herein compared to butylated hydroxytoluene (BHT), the values representing means of three replicates ±SD.

The sulindac derivatives are compounds of the formula:

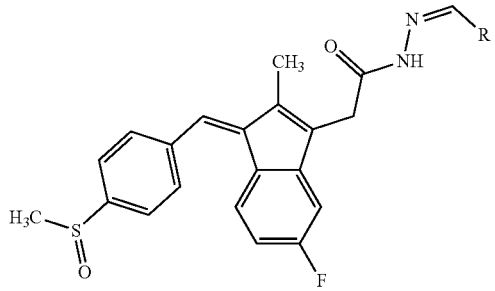

wherein R is selected from the group consisting of 2-nitrophenyl; 4-nitrophenyl; phenyl; 4-chlorophenyl; 3-hydroxyphenyl; 3-methoxyphenyl; 3-nitrophenyl; 4-dimethylaminophenyl; 2,4,5-trimethoxyphenyl; 3,4,5-trimethoxyphenyl; 4-hydroxyphenyl; 2-methoxyphenyl; 2,4-dimethoxyphenyl; 2,3-dimethoxyphenyl; 3,4-dimethoxyphenyl; 2,4,6-trimethoxyphenyl; 2,3,4-trimethoxyphenyl; 3-methoxy-4-ethoxyphenyl; 3,5-dimethoxy-4-hydroxyphenyl; 3-ethoxy-4-hydroxyphenyl; 2,5-dihydroxyphenyl; 3-hydroxy-4-methoxyphenyl; 2,3-dihydroxyphenyl; 2-hydroxy-3-methoxyphenyl; and 2,3,4-trihydroxyphenyl; and pharmaceutically acceptable salts thereof.

The sulindac derivatives are synthesized by refluxing sulindac hydrazide with appropriately substituted benzaldehydes in the presence of ethanol and catalytic amounts of glacial acetic acid, as described in detail herein.

The sulindac derivatives are N'-(substituted phenyl)-2-((1Z)-1-(4-(methylsulfinyl) benzylidene)-5-fluoro-2-methyl-1H-inden-3-yl) acetohydrazide derivatives or a pharmaceutically acceptable salt thereof.

The sulindac derivatives can be used as an active ingredient of a pharmaceutical for use in treating inflammation or inflammatory diseases.

The sulindac derivatives can be used as analgesic and/or gastric sparing agents.

Pharmaceutically acceptable salts include any non-toxic salt of the sulindac derivatives, which are generally prepared by reacting a free acid with a suitable organic or inorganic base. Examples of such salts include, but are not limited to, acetate, benzenesulfonate, benzoate, bicarbonate, bisulfate, bitartrate, borate, bromide, calcium, calcium edetate, camsylate, carbonate, chloride, clavulanate, citrate, dihydrochioride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamoate, palmitate, panthothenate, phosphate/diphosphate, polygalacturonate, potassium, salicylate, sodium, stearate, subacetate, succinate, tannate, tartrate, teoclate, tosylate, triethiodide, and valerate.

The present derivatives may be administered to a subject by any suitable route. For example, the present derivatives can be administered orally (including bucally and sublingually), nasally, rectally, parenterally, intracisternally, intra vaginally, intraperitoneally, topically and transdermally (as by powders, ointments, or drops). The term "parenteral" administration as used herein refers to modes of administration other than through the gastrointestinal tract, which include intravenous, intramuscular, intraperitoneal, intrasternal, intramammary, intraocular, retrobulbar, intrapulmonary, intrathecal, subcutaneous and intraarticular injection and infusion. Surgical implantation is also contemplated, including, for example, embedding a sulindac derivative composition in the body, for example, in a tissue, in the abdominal cavity, under the splenic capsule, brain, or in the cornea. Accordingly, the route of administration can include intranasal administration, oral administration, inhalation administration, subcutaneous administration, transdermal administration, intradermal administration, intra-arterial administration, with or without occlusion, intracranial administration, intraventricular administration, intravenous administration, buccal administration, intraperitoneal administration, intraocular administration, intramuscular administration, implantation administration, topical administration, intra-tumor administration and/or central venous administration.

It should be understood that the sulindac derivatives may be manufactured as, or incorporated into, pharmaceutical compositions including one or more of the present sulindac derivatives and/or pharmaceutically equivalent salts thereof. The present derivatives may be intimately admixed with a pharmaceutically acceptable carrier according to conventional pharmaceutical compounding techniques. Carriers, as used herein, are inert pharmaceutical excipients, including, but not limited to, binders, suspending agents, lubricants, flavorings, sweeteners, preservatives, dyes, and coatings. In preparing compositions in oral dosage form, any suitable type of pharmaceutical carrier may be employed. For example, for liquid oral preparations, suitable carriers and additives include water, glycols, oils, alcohols, flavoring agents, preservatives, coloring agents and the like; and for solid oral preparations, suitable carriers and additives include starches, sugars, diluents, granulating agents, lubricants, binders, disintegrating agents and the like. For parenteral use, the carrier is typically sterile water, although other ingredients, for example, for purposes such as aiding solubility or for preservation, may be included. Injectable suspensions may also be prepared, in which case appropriate liquid carriers, suspending agents and the like may be employed. For example, the pharmaceutically acceptable carrier can include alcohol, dimethyl sulfoxide (DMSO), a physiological saline, a lipid-based formulation, a liposomal formulation, a nanoparticle formulation, a micellar formulation, a water soluble formulation, a biodegradable polymer, an aqueous preparation, a hydrophobic preparation, a lipid-based vehicle, or a polymer formulation.

As a further alternative, the derivatives may be administered in the form of liposomes. Liposomes generally are derived from phospholipids or other lipid substances. Liposomes are formed by mono- or multi-lamellar hydrated liquid crystals that are dispersed in an aqueous medium. Any nontoxic, physiologically acceptable and metabolizable lipid capable of forming liposomes can be used. The present compositions in liposome form may contain, in addition to a sulindac derivative, stabilizers, preservatives, excipients and the like. Exemplary lipids include phospholipids and the phosphatidyl cholines (lecithins), both natural and synthetic.

Pharmaceutical compositions for parenteral injection can include pharmaceutically acceptable sterile aqueous or nonaqueous solutions, dispersions, suspensions, or emulsions, as well as sterile powders for reconstitution into sterile injectable solutions or dispersions just prior to use. Examples of suitable aqueous and nonaqueous carriers, diluents, solvents, or vehicles include water, ethanol, polyols (such as, glycerol, propylene glycol, polyethylene glycol, and the like), and suitable mixtures thereof, vegetable oils (such, as olive oil), and injectable organic esters, such as ethyl oleate. Proper fluidity can be maintained, for example, by the use of coating materials, such as lecithin, by the maintenance of the required particle size in the case of dispersions, and by the use of surfactants.

The present compositions may include adjuvants, such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It also may be desirable to include isotonic agents, such as sugars, sodium chloride and the like. Prolonged absorption of the injectable pharmaceutical form can be brought about by the inclusion of agents that delay absorption, such as aluminum monostearate and gelatin. In some cases, in order to prolong the effect of the drug, it is desirable to slow the absorption of the drug from subcutaneous or intramuscular injection. This result can be accomplished by the use of a liquid suspension of crystalline or amorphous materials with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

The present compositions can be provided in unit dosage forms, such as tablets, pills, capsules, powders, granules, ointments, sterile parenteral solutions or suspensions, metered aerosol or liquid sprays, drops, ampules, auto-injector devices or suppositories, for oral parenteral, intra-nasal, sublingual or rectal administration, or for administration by inhalation or insufflation. The active compound is mixed under sterile conditions with a pharmaceutically acceptable carrier and any needed preservatives, buffers, or propellants that may be required. Ophthalmic formulations, eye ointments, powders, and solutions are also contemplated. The composition can be presented in a form suitable for daily, weekly or monthly administration. The pharmaceutical compositions will contain, per dosage unit, e.g., tablet, capsule, powder, injection, teaspoonful, suppository and the like, an amount of the active ingredient necessary to deliver an effective dose. A therapeutically effective amount of the sulindac derivatives or an amount effective to treat inflammation may be determined initially from in vivo assays described herein, and adjusted for specific desired present derivatives using routine methods.

The following examples further illustrate the present teachings.

Example 1

Synthesis of Sulindac Derivatives

The N'-(substituted phenyl)-2-(1Z)-1-(4-(methylsulfinyl) benzylidene)-5-fluoro-2-methyl-1H-inden-3-yl) acetohydrazide derivatives may be synthesized according to the reaction scheme shown in FIG. 2. The hydrazide, 2-[(1Z)-5-fluoro-1-{[4-(methanesulfinyl) phenyl] methylidene}-2-methyl-1H-inden-3-yl] acetohydrazide was synthesized by refluxing the methyl ester of sulindac and hydrazine hydrate (99%) in the presence of absolute ethanol. The resulting hydrazide was refluxed with selected substituted benzaldehydes in the presence of ethanol and a catalytic amount of glacial acetic acid. Twenty five different sulindac derivative compounds were synthesized (FIG. 2). The structures of all synthesized compounds were assigned on the basis of elemental analysis, as well as FT IR, $^1$H NMR, $^{13}$C NMR, and mass spectral data.

Sulindac methyl ester (0.01 mol) and hydrazine hydrate (99%) (p.2 mol) were refluxed in absolute ethanol (50 mL) for 30 hours. The mixture was concentrated, cooled, and poured in crushed ice in small portions while stirring, and kept for 3-4 hours at room temperature. A separated solid was filtered out, dried, and crystallized from ethanol. The product was checked by thin layer chromatography.

The resulting compound (compound [III] in FIG. 2) is 2-[(1Z)-5-fluoro-1-{[4-(methanesulfinyl)phenyl]methylidene}-2-methyl-1H-inden-3-yl]acetohydrazide. Color: yellow; Yield: 70%; m.p.: 120-122° C.; UV λmax (Methanol)= 327 nm; $^1$H NMR (500 MHz, DMSO-$d_6$): δ=2.20 (3H, s, CH$_3$), 2.82 (3H, s, SOCH$_3$), 3.38 (2H, s, CH$_2$), 4.28 (2H, bs, NH$_2$, D$_2$O exchg.), 6.71 (1H, t, J=9.5 Hz, =CH), 7.15-7.80 (7H, m, Ar—H), 9.30 (1H, bs, CONH, D$_2$O exchg.); $^{13}$C NMR (125.76 MHz, DMSO-$d_6$): δ=10.88, 31.39, 43.59, 106.74, 106.93, 110.69, 110.87, 123.49, 123.56, 124.39, 129.71, 129.93, 130.40, 133.86, 138.29, 139.07, 140.95, 140.95, 146.69, 147.62, 147.69, 162.63, 163.96, 168.69; MS: m/z=370.44 [M]$^+$; Analysis: for C$_{20}$H$_{19}$FN$_2$O$_2$S, calcd. C, 64.85, H, 5.17, N, 7.56, S, 8.66%; found C, 64.65, H, 5.15, N, 7.54 S, 8.88%.

To prepare other N'-(substituted benzylidene)-2-((1Z)-1-(4-(methylsulfinyl) benzylidene)-5-fluoro-2-methyl-1H-inden-3-yl) acetohydrazide derivatives (1-25), a solution of sulindac hydrazide (1.0 mmol) in EtOH (15 mL) containing appropriate substituted benzaldehydes (1.1 mmol) and a catalytic amount of glacial acetic acid was heated under reflux for 3 hours. The reaction mixture was added to the ice cold water in a beaker. The product was precipitated, filtered by vacuum filtration and washed several times with cold water. The solid was recrystallized from ethanol.

2-[(1 Z)-5-fluoro-1-{[4-(methanesulfinyl) phenyl] methylidene}-2-methyl-1H-inden-3-yl] acetohydrazide (compound [iii] of FIG. 2) was used as a starting material for the synthesis of various substituted sulindac derivatives. Schiff bases were obtained by refluxing sulindac hydrazide with differently substituted benzaldehydes in ethanol with glacial acetic acid as catalyst. The synthesis of these compounds was achieved through an efficient synthetic route. $^1$H-NMR and $^{13}$C-NMR were used to confirm the structures of the synthesized compounds. The structures were also characterized by elemental analysis, mass spectrometry and FT-IR. 2-[(1Z)-5-fluoro-1-{[4-(methanesulfinyl) phenyl] methylidene}-2-methyl-1H-inden-3-yl] acetohydrazide demonstrated a similar NMR splitting pattern and δ-values ($δ_H$ & $δ_C$) as that of sulindac. The structures of the sulindac hydrazide derivatives were established on the basis of $^1$H-NMR analysis, which was confirmed by the disappearance of —NH$_2$ protons at 4.28 ppm. The presence of all carbon atoms for compounds (1-25) was confirmed by the $^{13}$C-NMR spectra. Molecular weights of compounds were confirmed by mass spectra. Molecular ion peaks were observed in all the compounds.

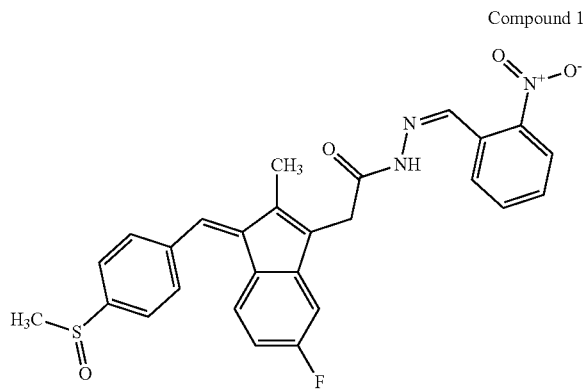 [SMILES: CC1=C(CC(=O)N/N=C\c2ccccc2[N+](=O)[O-])c2cc(F)ccc2/C1=C\c1ccc(S(C)=O)cc1]

Compound 1

N'-(2-nitrobenzylidene)-2-((1Z)-1-(4-(methylsulfinyl) benzylidene)-5-fluoro-2-methyl-1H-inden-3-yl)acetohydrazide (1). Yield: 70%; m. p.: 148-150° C.; IR (KBr) cm$^{-1}$: 3001 (NH str.), 1665 (C=O, Str.), 1570 (C=N str.); $^1$H NMR (500 MHz, DMSO-$d_6$): δ=2.23 (3H, s, CH$_3$), 2.82 (3H, s, S=OCH$_3$), 3.62 (1H, s, CH$_2$), 4.00 (1H, s, CH$_2$), 6.71 (1H, s, =CH), 7.06-8.08 (11H, m, Ar—H), 8.42 (1H, s, N=CH), 11.79 (1H, s, CONH, D$_2$O exchg.); $^{13}$C NMR (125.76 MHz, DMSO-$d_6$): δ=10.9, 29.9, 43.5, 124.4, 125.0, 128.7, 129.7, 129.8, 130.4, 130.9, 133.9, 138.5, 139.0, 139.2, 140.8, 142.6, 147.7, 148.4, 171.8; MS: m/z=503.22

[M]$^+$; Analysis: for $C_{27}H_{22}FN_3O_4S$, calcd. C, 64.40, H, 4.40, N, 8.34, S, 6.37%; found C, 64.60, H, 4.41, N, 8.36, S, 6.39%.

Compound 2

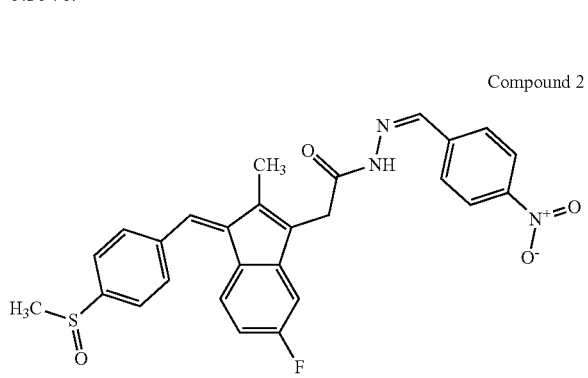

N'-(4-nitrobenzylidene)-2-((1Z)-1-(4-(methylsulfinyl) benzylidene)-5-fluoro-2-methyl-1H-inden-3-yl)acetohydrazide (2) Yield: 80%; m. p.: 220-222° C.; IR (KBr) cm$^{-1}$: 2962 (NH str.), 1666 (C=O, Str.), 1591 (C=N str.); $^1$H NMR (500 MHz, DMSO-d$_6$): δ=2.23 (3H, s, CH$_3$), 2.82 (3H, s, S=OCH$_3$), 3.64 (1H, s, CH$_2$), 4.00 (1H, s, CH$_2$), 6.71 (1H, s, =CH), 7.08-7.97 (11H, m, Ar—H), 8.38 (1H, s, N=CH), 11.80 (1H, s, CONH, D$_2$O exchg.); $^{13}$C NMR (125.76 MHz, DMSO-d$_6$): δ=10.9, 29.8, 32.0, 43.5, 124.3, 124.4, 128.2, 128.4, 129.8, 130.4, 139.0, 140.8, 141.4, 146.6, 148.1, 166.3, 171.9; MS: m/z=504.28 [M+1]$^+$; Analysis: for $C_{27}H_{22}FN_3O_4S$, calcd. C, 64.40, H, 4.40, N, 8.34, S, 6.37%; found C, 64.62, H, 4.39, N, 8.36, S, 6.38%.

Compound 3

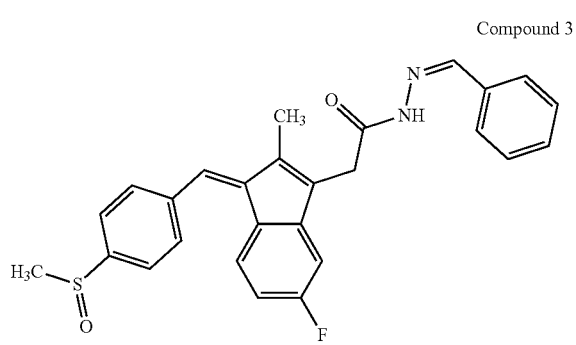 [SMILES: CC1=C(CC(=O)N/N=C\c2ccccc2)c2cc(F)ccc2/C1=C\c1ccc(S(C)=O)cc1]

2-(1Z)-1-(4-(methylsulfinyl)benzylidene)-5-fluoro-2-methyl-1H-inden-3-yl)-N'-benzylideneacetohydrazide (3): Yield: 65%; m. p.: 138-140° C.; IR (KBr) cm$^{-1}$: 2980 (NH str.), 1662 (C=O, Str.), 1591 (C=N str.); $^1$H NMR (500 MHz, DMSO-d$_6$): δ=2.23 (3H, s, CH$_3$), 2.82 (3H, s, S=OCH$_3$), 3.59 (1H, s, CH$_2$), 4.00 (1H, s, CH$_2$), 6.71 (1H, s, =CH), 7.11-7.78 (12H, m, Ar—H), 8.28 (1H, s, N=CH), 11.50 (1H, s, CONH, D$_2$O exchg.); $^{13}$C NMR (125.76 MHz, DMSO-d$_6$): δ=10.9, 29.9, 43.5, 124.3, 127.3, 127.5, 129.0, 129.2, 129.7, 129.9, 130.0, 130.3, 130.4, 134.6, 138.4, 139.0, 140.9, 143.8, 146.6, 171.5; MS: m/z=459.39 [M+1]$^+$; Analysis: for $C_{27}H_{23}FN_2O_2S$, calcd. C, 70.72, H, 5.06, N, 6.11, S, 6.99%; found C, 70.99, H, 5.05, N, 6.14, S, 6.97%.

Compound 4

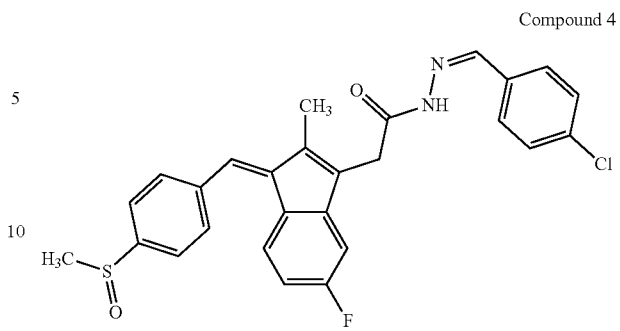

N'-(4-chlorobenzylidene)-2-((1Z)-1-(4-(methylsulfinyl) benzylidene)-5-fluoro-2-methyl-1H-inden-3-yl)acetohydrazide (4): Yield: 85%; m. p.: 228-230° C.; IR (KBr) cm$^{-1}$: 2955 (NH str.), 1664 (C=O, Str.), 1599 (C=N str.); $^1$H NMR (500 MHz, DMSO-d$_6$): δ=2.22 (3H, s, CH$_3$), 2.82 (3H, s, S=OCH$_3$), 4.00 (2H, s, CH$_2$), 6.72 (1H, s, =CH), 7.09-7.78 (11H, m, Ar—H), 8.27 (1H, s, N=CH), 11.56 (1H, s, CONH, D$_2$O exchg.); $^{13}$C NMR (125.76 MHz, DMSO-d$_6$): δ=10.9, 29.9, 43.5, 124.3, 128.9, 129.3, 129.7, 130.4, 134.7, 139.0, 146.7, 171.5; MS: m/z=493.40 [M+1]$^+$; Analysis: for $C_{27}H_{22}ClFN_2O_2S$, calcd. C, 65.78, H, 4.50, N, 5.68, S, 6.50%; found C, 65.55, H, 4.49, N, 6.48, S, 6.52%.

Compound 5

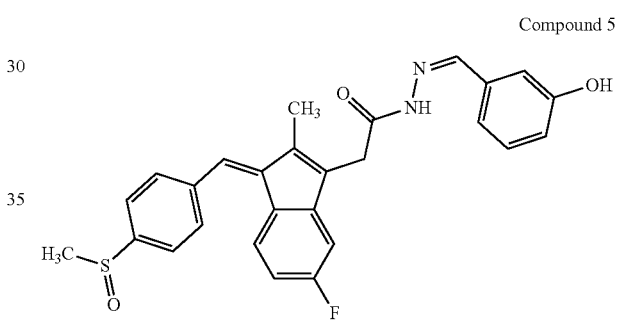

N'-(3-hydroxybenzylidene)-2-(1Z)-1-(4-(methylsulfinyl) benzylidene)-5-fluoro-2-methyl-1H-inden-3-yl)acetohydrazide (5): Yield: 60%; m. p.: 240-242° C.; IR (KBr) cm$^{-1}$: 3080 (NH str.), 1664 (C=O, Str.), 1601 (C=N str.); $^1$H NMR (500 MHz, DMSO-d$_6$): δ=2.22 (3H, s, CH$_3$), 2.81 (3H, s, CH$_3$S=O), 3.99 (1H, s, CH$_2$), 6.71 (1H, s, =CH), 7.10-7.97 (11H, m, Ar—H), 8.10 (1H, s, N=CH), 9.65 (1H, s, OH, D$_2$O exchg.), 11.44 (1H, s, CONH, D$_2$O exchg.); $^{13}$C NMR (125.76 MHz, DMSO-d$_6$): δ=10.9, 29.7, 43.5, 110.7, 113.2, 118.7, 124.3, 129.9, 130.4, 135.8, 140.9, 144.0, 158.1, 171.4; MS: m/z=474.94 [M]$^+$; Analysis: for $C_{27}H_{23}FN_2O_3S$, calcd. C, 68.34, H, 4.89, N, 5.90, S, 6.76%; found C, 68.07, H, 4.90, N, 5.88, S, 6.78%.

Compound 6

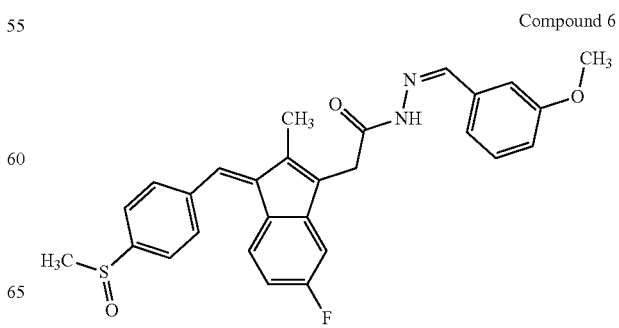

N'-(3-methoxybenzylidene)-2-(1Z)-1-(4-(methylsulfinyl)benzylidene)-5-fluoro-2-methyl-1H-inden-3-yl)acetohydrazide (6): Yield: 65%; m. p.: 130-132° C.; IR (KBr) cm$^{-1}$: 2960 (NH str.), 1664 (C=O, Str.), 1588 (C=N str.); $^1$H NMR (500 MHz, DMSO-d$_6$): δ=2.22 (3H, s, CH$_3$), 2.82 (3H, s, CH$_3$S=O), 3.79 (3H, s, OCH$_3$), 4.01 (2H, s, CH$_2$), 6.76 (1H, s, =CH), 6.99-7.78 (11H, m, Ar—H), 8.03 (1H, s, N=CH), 11.52 (1H, s, CONH, D$_2$O exchg.); $^{13}$C NMR (125.76 MHz, DMSO-d$_6$): δ=10.9, 11.0, 29.9, 43.5, 55.5, 93.0, 110.8, 116.3, 120.0, 123.5, 124.3, 129.9, 130.4, 133.7, 136.0, 138.4, 138.7, 139.0, 140.9, 143.7, 146.6, 147.1, 160.0, 171.5; MS: m/z=488.85 [M]$^+$; Analysis: for C$_{28}$H$_{25}$FN$_2$O$_3$S, calcd. C, 68.83, H, 5.16, N, 5.73, S, 6.56%; found C, 69.10, H, 5.17, N, 5.75, S, 6.54%.

Compound 7

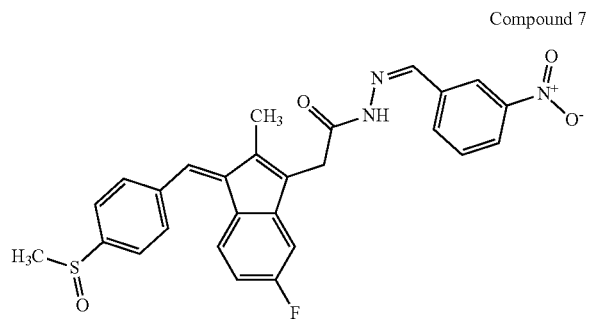 [SMILES: CC1=C(CC(=O)N/N=C\c2cccc([N+](=O)[O-])c2)c2cc(F)ccc2/C1=C\c1ccc(S(C)=O)cc1]

N'-(3-nitrobenzylidene)-2-(1Z)-1-(4-(methylsulfinyl)benzylidene)-5-fluoro-2-methyl-1H-inden-3-yl)acetohydrazide (7): Yield: 70%; m. p.: 165-167° C.; IR (KBr) cm$^{-1}$: 3002 (NH str.), 1654 (C=O, Str.), 1570 (C=N str.); $^1$H NMR (500 MHz, DMSO-d$_6$): δ=2.21 (3H, s, CH$_3$), 2.82 (3H, s, S=O CH$_3$), 3.63 (1H, s, CH$_2$), 4.03 (1H, s, CH$_2$), 6.70 (1H, s, =CH), 7.08-8.24 (11H, m, Ar—H), 8.52 (1H, s, N=CH), 11.73 (1H, s, CONH, D$_2$O exchg.); $^{13}$C NMR (125.76 MHz, DMSO-d$_6$): δ=10.9, 30.0, 43.5, 121.4, 124.3, 124.5, 129.7, 129.8, 130.4, 130.8, 133.4, 136.4, 138.4, 139.0, 140.8, 141.6, 146.6, 148.6, 171.8; MS: m/z=504.41 [M+1]$^+$; Analysis: for C$_{27}$H$_{23}$FN$_2$O$_2$S, calcd. C, 70.72, H, 5.06, N, 6.11, S, 6.99%; found C, 71.00, H, 5.07, N, 6.14, S, 6.97%.

Compound 8

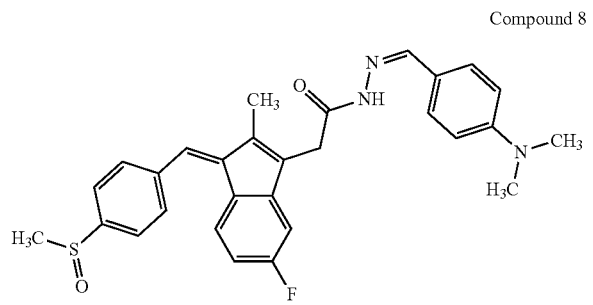

N'-(4-dimethylaminobenzylidene)-2-(1Z)-1-(4-(methylsulfinyl)benzylidene)-5-fluoro-2-methyl-1H-inden-3-yl)acetohydrazide (8): Yield: 50%; m. p.: 158-160° C.; IR (KBr) cm$^{-1}$: 3025 (NH str.), 1655 (C=O, Str.), 1599 (C=N str.); $^1$H NMR (500 MHz, DMSO-d$_6$): δ=2.22 (3H, s, CH$_3$), 2.82 (3H, s, S=O CH$_3$), 2.96 (6H, s, 2×NCH$_3$), 3.54 (1H, s, CH$_2$), 3.96 (1H, s, CH$_2$), 6.73 (1H, s, =CH), 7.12-7.92 (11H, m, Ar—H), 8.12 (1H, s, N=CH), 11.19 (1H, s, CONH, D$_2$O exchg.); $^{13}$C NMR (125.76 MHz, DMSO-d$_6$): δ=11.0, 29.9, 43.5, 112.2, 124.3, 128.5, 128.8, 129.6, 129.9, 130.4, 144.7, 146.6, 170.8; MS: m/z=501.77 [M]$^+$; Analysis: for C$_{29}$H$_{28}$FN$_3$O$_2$S, calcd. C, 69.44, H, 5.63, N, 8.38, S, 6.39%; found C, 69.17, H, 5.62, N, 8.35, S, 6.41%.

Compound 9

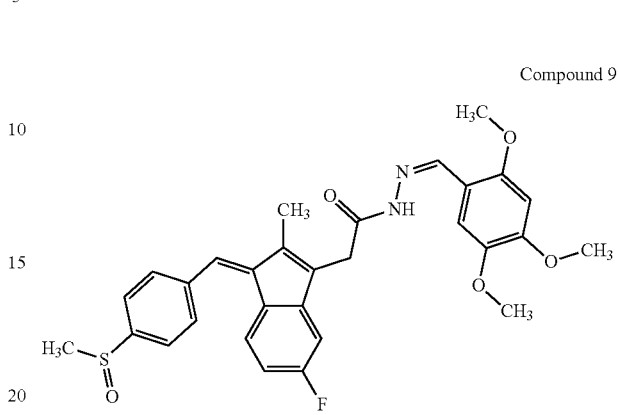

N'-(2,4,5-trimethoxybenzylidene)-2-(1Z)-1-(4-(methylsulfinyl)benzylidene)-5-fluoro-2-methyl-1H-inden-3-yl)acetohydrazide (9): Yield: 60%; m. p.: 233-235° C.; IR (KBr) cm$^{-1}$: 2914 (NH str.), 1658 (C=O, Str.), 1598 (C=N str.); $^1$H NMR (500 MHz, DMSO-d$_6$): δ=2.19 (3H, s, CH$_3$), 2.81 (3H, s, S=OCH$_3$), 3.78 (9H, s, 3×OCH$_3$), 3.84 (2H, s, CH$_2$), 6.25 (1H, s, =CH), 7.19-7.72 (9H, m, Ar—H), 8.22 (1H, s, N=CH), 11.11 (1H, s, CONH, D$_2$O exchg.); MS: m/z=544.67 [M−4]$^+$; Analysis: for C$_{30}$H$_{29}$FN$_2$O$_5$S, calcd. C, 65.68, H, 5.33, N, 5.11, S, 5.84%; found C, 65.45, H, 5.32, N, 5.09, S, 5.85%.

Compound 10

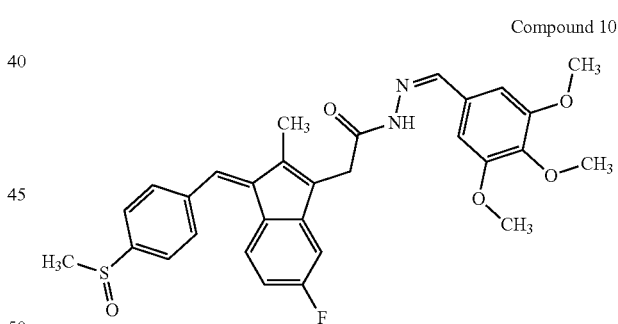

N'-(3,4,5-trimethoxybenzylidene)-2-((1Z)-1-(4-(methylsulfinyl)benzylidene)-5-fluoro-2-methyl-1H-inden-3-yl)acetohydrazide (10): Yield: 62%; m. p.: 165-167° C.; IR (KBr) cm$^{-1}$: 2917 (NH str.), 1652 (C=O, Str.), 1598 (C=N str.); $^1$H NMR (500 MHz, DMSO-d$_6$): δ=2.20 (3H, s, CH$_3$), 2.82 (3H, s, S=OCH$_3$), 3.75 (9H, s, 3×OCH$_3$), 4.01 (1H, s, CH$_2$), 6.69 (1H, s, =CH), 7.01-7.75 (9H, m, Ar—H), 8.03 (1H, s, N=CH), 11.53 (1H, s, CONH, D$_2$O exchg.); $^{13}$C NMR (125.76 MHz, DMSO-d$_6$): δ=11.2, 30.2, 43.6, 56.4, 60.7, 104.6, 107.0, 110.9, 123.6, 124.5, 130.0, 130.5, 133.8, 138.8, 139.1, 139.5, 140.9, 143.9, 146.7, 147.3, 147.7, 153.7, 162.4, 163.7, 171.6; MS: m/z=547.64 [M−1]$^+$; Analysis: for C$_{30}$H$_{29}$FN$_2$O$_5$S, calcd. C, 65.68, H, 5.33, N, 5.11, S, 5.84%; found C, 65.43, H, 5.32, N, 5.13, S, 5.82%.

Compound 11

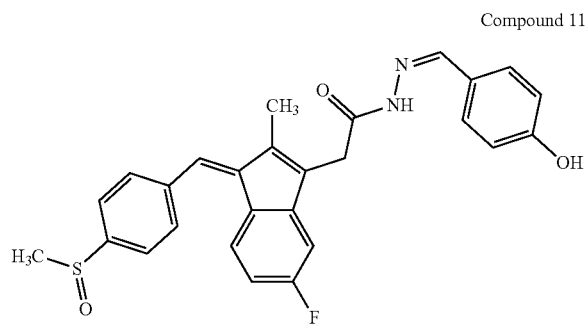 [SMILES: CC1=C(CC(=O)N/N=C\c2ccc(O)cc2)c2cc(F)ccc2/C1=C\c1ccc(S(C)=O)cc1]

N'-(4-hydroxybenzylidene)-2-((1Z)-1-(4-(methylsulfinyl)benzylidene)-5-fluoro-2-methyl-1H-inden-3-yl)acetohydrazide (11): Yield: 50%; m. p.: 210-212° C.; IR (KBr) cm$^{-1}$: 3031 (NH str.), 1652 (C=O, Str.), 1597 (C=N str.); $^1$H NMR (500 MHz, DMSO-d$_6$): δ=2.22 (3H, s, CH$_3$), 2.82 (3H, s, S=OCH$_3$), 3.17 (1H, s, CH$_2$), 3.96 (1H, s, CH$_2$), 6.71 (1H, s, =CH), 6.81-7.94 (11H, m, Ar—H), 8.16 (1H, s, N=CH), 9.90 (1H, s, —OH), 11.28 (1H, s, CONH, D$_2$O exchg.); $^{13}$C NMR (125.76 MHz, DMSO-d$_6$): δ=11.0, 29.9, 43.5, 49.0, 106.8, 110.8, 116.1, 124.4, 129.0, 130.4, 144.1, 146.6, 147.4, 147.8, 147.9, 159.6, 159.8, 162.2, 163.6, 165.4, 171.1; MS: m/z=474.75 [M]'; Analysis: for C$_{27}$H$_{23}$FN$_2$O$_3$S, calcd. C, 68.34, H, 4.89, N, 5.90, S, 6.76%; found C, 68.12, H, 4.90, N, 5.91, S, 6.75%.

Compound 13

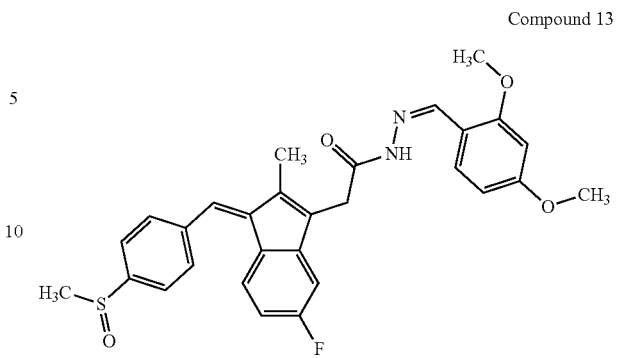

N'-(2,4-dimethoxybenzylidene)-2-((1Z)-1-(4-(methylsulfinyl)benzylidene)-5-fluoro-2-methyl-1H-inden-3-yl)acetohydrazide (13): Yield: 60%; m. p.: 185-187° C.; IR (KBr) cm$^{-1}$: 3011 (NH str.), 1654 (C=O, Str.), 1600 (C=N str.); NMR (500 MHz, DMSO-d$_6$): δ=2.21 (3H, s, CH$_3$), 2.79 (3H, s, S=OCH$_3$), 3.81 (6H, s, 2×CH$_3$), 3.85 (2H, s, CH$_2$), 6.63 (1H, s, =CH), 7.12-7.75 (10H, m, Ar—H), 8.33 (1H, s, N=CH), 11.32 (1H, s, CONH, D$_2$O exchg.); $^{13}$C NMR (125.76 MHz, DMSO-d$_6$): δ=10.9, 29.9, 32.0, 43.5, 55.8, 56.1, 98.5, 106.7, 110.7, 115.3, 123.4, 124.3, 127.0, 129.5, 130.3, 133.4, 138.2, 139.0, 140.8, 142.6, 147.5, 159.4, 162.2, 163.6, 165.4, 171.1; MS: m/z=518.91 [M]$^+$; Analysis: for C$_{29}$H$_{27}$FN$_2$O$_4$S, calcd. C, 67.16, H, 5.25, N, 5.40, S, 6.18%; found C, 67.33, H, 5.26, N, 5.42, S, 6.17%.

Compound 14

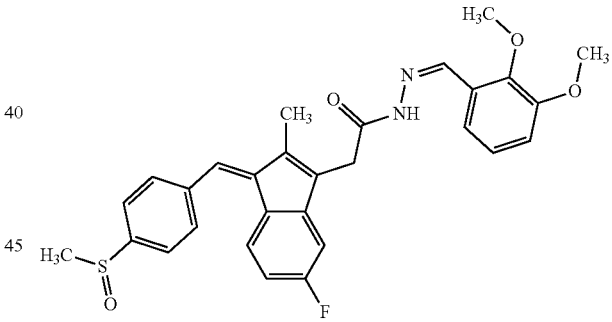

Compound 12

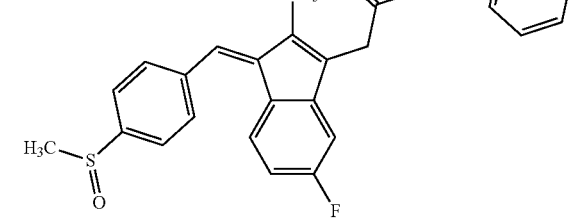

N'-(2-methoxybenzylidene)-2-((1Z)-1-(4-(methylsulfinyl) benzylidene)-5-fluoro-2-methyl-1H-inden-3-yl) acetohydrazide (12): Yield: 55%; m. p.: 173-176° C.; IR (KBr) cm$^{-1}$: 3007 (NH str.), 1653 (C=O, Str.), 1564 (C=N str.); $^1$H NMR (500 MHz, DMSO-d$_6$): δ=2.18 (3H, s, CH$_3$), 2.79 (3H, s, S=OCH$_3$), 3.81 (3H, s, OCH$_3$), 3.95 (2H, s, CH$_2$), 6.67 (1H, s, =CH), 6.97-7.83 (11H, m, Ar—H), 8.36 (1H, s, N=CH), 11.43 (1H, s, CONH, D$_2$O exchg.); MS: m/z=489.45 [M+1]$^+$; Analysis: for C$_{28}$H$_{25}$FN$_2$O$_3$S, calcd. C, 68.83, H, 5.16, N, 5.73, S, 6.56%; found C, 68.56, H, 5.15, N, 5.75, S, 5.13%.

N'-(2,3-dimethoxybenzylidene)-2-((1Z)-1-(4-(methylsulfinyl)benzylidene)-5-fluoro-2-methyl-1H-inden-3-yl)acetohydrazide (14): Yield: 62%; m. p.: 203-205° C.; IR (KBr) cm$^{-1}$: 3014 (NH str.), 1654 (C=O, Str.), 1565 (C=N str.); $^1$H NMR (500 MHz, DMSO-d$_6$): δ=2.20 (3H, s, CH$_3$), 2.82 (3H, s, S=OCH$_3$), 3.58 (1H, s, CH$_2$), 3.79 (6H, s, 2×OCH$_3$), 3.99 (1H, s, CH$_2$), 6.71 (1H, s, =CH), 7.09-7.80 (10H, m, Ar—H), 8.30 (1H, s, N=CH), 11.47 (1H, s, CONH, D$_2$O exchg.); $^{13}$C NMR (125.76 MHz, DMSO-d$_6$): δ=10.9, 29.9, 32.0, 43.5, 56.2, 61.6, 106.7, 106.9, 110.7, 114.4, 117.3, 124.3, 130.4, 138.4, 139.0, 139.5, 140.9, 142.5, 146.6, 148.3, 153.1, 162.2, 163.6, 165.7, 171.4; MS: m/z=518.84 [M]$^+$; Analysis: for C$_{29}$H$_{27}$FN$_2$O$_4$S, calcd. C, 67.16, H, 5.25, N, 5.40, S, 6.18%; found C, 67.3.1, H, 5.24, N, 5.38, S, 6.19%.

Compound 15

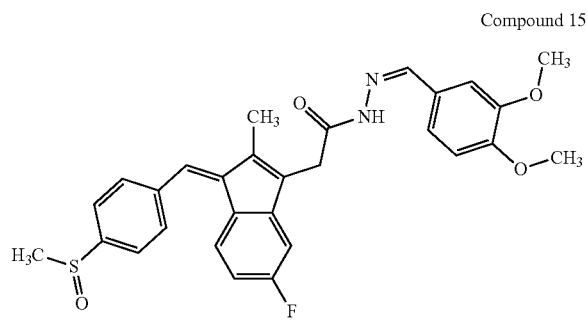

N'-(3,4-dimethoxybenzylidene)-2-((1Z)-1-(4-(methylsulfinyl)benzylidene)-5-fluoro-2-methyl-1H-inden-3-yl)acetohydrazide (15): Yield: 65%; m. p.: 230-232° C.; IR (KBr) cm$^{-1}$: 3002 (NH str.), 1656 (C=O, Str.), 1571 (C=N str.); $^1$H NMR (500 MHz, DMSO-d$_6$): δ=2.23 (3H, s, CH$_3$), 2.83 (3H, s, S=OCH$_3$), 3.57 (1H, s, CH$_2$), 3.79 (6H, s, 2×OCH$_3$), 4.00 (1H, s, CH$_2$), 6.71 (1H, s, =CH), 7.01-7.81 (10H, m, Ar—H), 7.98 (1H, s, N=CH), 11.38 (1H, s, CONH, D$_2$O exchg.); $^{13}$C NMR (125.76 MHz, DMSO-d$_6$): δ=10.9, 30.0, 32.0, 43.5, 55.8, 56.0, 108.7, 111.9, 121.8, 122.2, 124.4, 127.3, 129.8, 130.4, 138.3, 139.4, 138.3, 139.0, 140.8, 144.0, 146.6, 149.4, 150.9, 171.2; MS: m/z=518.58 [M]$^+$; Analysis: for C$_{29}$H$_{27}$FN$_2$O$_4$S, calcd. C, 67.16, H, 5.25, N, 5.40, S, 6.18%; found C, 67.32, H, 5.26, N, 5.38, S, 6.17%.

Compound 17

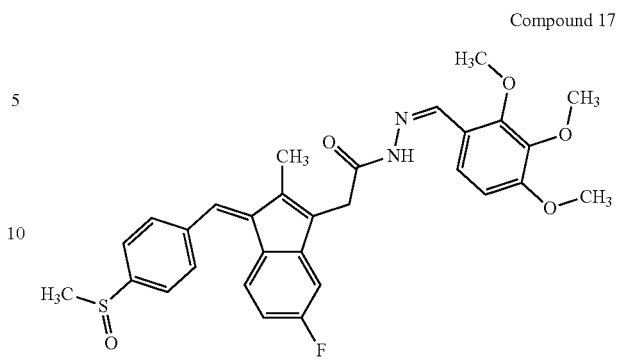

N'-(2,3,4-timethoxybenzylidene)-2-((1Z)-1-(4-(methylsulfinyl)benzylidene)-5-fluoro-2-methyl-1H-inden-3-yl)acetohydrazide (17): Yield: 70%; m. p.: 185-187° C.; IR (KBr) cm$^{-1}$: 2987 (NH str.), 1651 (C=O, Str.), 1589 (C=N str.); $^1$H NMR (500 MHz, DMSO-d$_6$): δ=2.18 (3H, s, CH$_3$), 2.80 (3H, s, S=OCH$_3$), 3.77 (9H, s, 3×OCH$_3$), 3.85 (2H, s, CH$_2$), 6.25 (1H, s, =CH), 7.19-7.72 (9H, m, Ar—H), 8.22 (1H, s, N=CH), 11.11 (1H, s, CONH, D$_2$O exchg.); $^{13}$C NMR (125.76 MHz, DMSO-d$_6$): δ=11.0, 30.0, 32.1, 43.6, 56.5, 61.0, 62.3, 106.9, 109.2, 110.9, 121.0, 124.5, 130.0, 130.5, 138.4, 139.1, 139.8, 141.0, 142.1, 142.6, 146.7, 153.0, 155.5, 162.3, 163.7, 165.6, 171.3; MS: m/z=548.03 [M]$^+$; Analysis: for C$_{30}$H$_{29}$FN$_2$O$_5$S, calcd. C, 65.68, H, 5.33, N, 5.11, S, 5.84%; found C, 65.45, H, 5.34, N, 5.13, S, 5.85%.

Compound 16

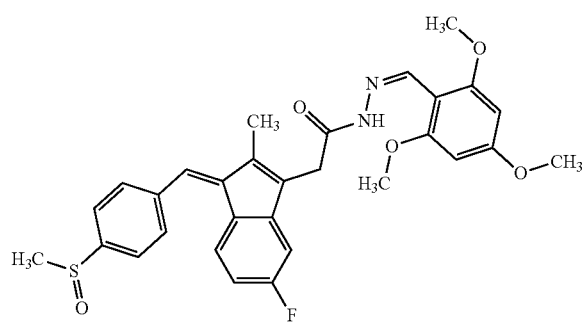

N'-(2,4,6-timethoxybenzylidene)-2-((1Z)-1-(4-(methylsulfinyl)benzylidene)-5-fluoro-2-methyl-1H-inden-3-yl)acetohydrazide (16): Yield: 68%; m. p.: 193-195° C.; IR (KBr) cm$^{-1}$: 3001 (NH str.), 1652 (C=O, Str.), 1584 (C=N str.); $^1$H NMR (500 MHz, DMSO-d$_6$): δ=2.19 (3H, s, CH$_3$), 2.79 (3H, s, S=OCH$_3$), 3.78 (9H, s, 3×OCH$_3$), 3.85 (2H, s, CH$_2$), 6.25 (1H, s, =CH), 7.18-7.72 (9H, m, Ar—H), 8.22 (1H, s, N=CH), 11.11 (1H, s, CONH, D$_2$O exchg.); $^{13}$C NMR (125.76 MHz, DMSO-d$_6$): δ=10.86, 29.38, 32.0, 43.5, 55.8, 56.3, 91.5, 104.1, 106.8, 110.8, 123.5, 124.4, 129.6, 130.4, 138.6, 139.1, 141.0, 142.9, 146.5, 147.9, 160.3, 162.3, 162.7, 163.7, 171.1; MS: m/z=547.97 [M−1]$^+$; Analysis: for C$_{30}$H$_{29}$FN$_2$O$_5$S, calcd. C, 65.68, H, 5.33, N, 5.11, S, 5.84%; found C, 65.88, H, 5.34, N, 5.13, S, 5.85%.

Compound 18

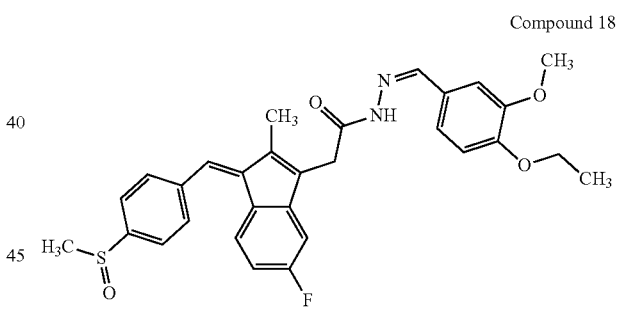

N'-(3-methoxy-4-ethoxybenzylidene)-2-((1Z)-1-(4-(methylsulfinyl)benzylidene)-5-fluoro-2-methyl-1H-inden-3-yl)acetohydrazide (18): Yield: 65%; m. p.: 158-160° C.; IR (KBr) cm$^{-1}$: 3227 (NH str.), 1658 (C=O, Str.), 1603 (C=N str.); $^1$H NMR (500 MHz, DMSO-d$_6$): δ=1.37 (3H, s, CH$_3$), 2.20 (3H, s, CH$_3$), 2.79 (3H, s, S=OCH$_3$), 3.76 (3H, s, OCH$_3$), 3.97 (2H, q, OCH$_2$), 4.01 (1H, s, CH$_2$), 6.70 (1H, s, =CH), 6.95-7.95 (10H, m, Ar—H), 8.16 (1H, s, N=CH), 11.36 (1H, s, CONH, D$_2$O exchg.); $^{13}$C NMR (125.76 MHz, DMSO-d6): δ=10.9, 11.0, 15.1, 30.0, 43.5, 55.7, 64.1, 106.8, 108.7, 110.7, 120.6, 121.7, 124.4, 127.1, 129.9, 130.4, 133.7, 138.3, 138.7, 139.0, 140.9, 144.0, 146.6, 147.4, 147.8, 149.5, 150.3, 162.2, 163.6, 165.6, 171.2; MS: m/z=535.19 [M+2]$^+$; Analysis: for C$_{30}$H$_{29}$FN$_2$O$_4$S, calcd. C, 67.65, H, 5.49, N, 5.26, S, 6.02%; found C, 67.42, H, 5.50, N, 5.24, S, 6.01%.

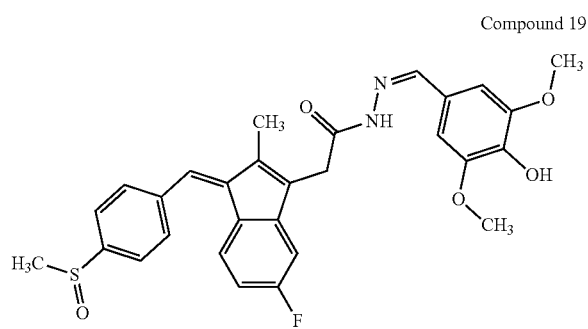

Compound 19

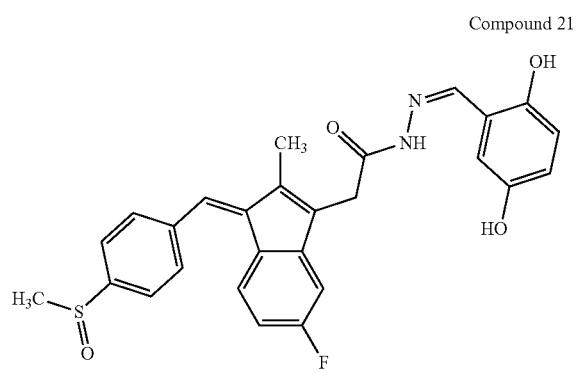 [SMILES: CC1=C(CC(=O)N/N=C\c2cc(O)ccc2O)c2cc(F)ccc2/C1=C\c1ccc(S(C)=O)cc1]

Compound 21

N'-(3,5-dimethoxy-4-hydroxybenzylidene)-2-((1Z)-1-(4-(methylsulfinyl)benzylidene)-5-fluoro-2-methyl-1H-inden-3-yl)acetohydrazide (19): Yield: 65%; m. p.: 218-220° C.; IR (KBr) cm$^{-1}$: 3010 (NH str.), 1654 (C=O, Str.), 1577 (C=N str.); $^1$H NMR (500 MHz, DMSO-d$_6$): δ=2.22 (3H, s, CH$_3$), 2.82 (3H, s, S=OCH$_3$), 3.84 (6H, s, 2×OCH$_3$), 3.98 (2H, s, CH$_2$), 6.72 (1H, s, =CH), 7.15-7.80 (9H, m, Ar—H), 8.33 (1H, s, N=CH), 11.31 (1H, s, CONH, D$_2$O exchg.); $^{13}$C NMR (125.76 MHz, DMSO-d$_6$): δ=10.9, 30.1, 43.5, 56.2, 56.9, 98.2, 106.8, 107.9, 108.3, 110.7, 113.6, 124.3, 130.4, 138.3, 139.0, 140.8, 142.7, 143.6, 146.6, 152.2, 153.6, 165.3, 171.1; MS: m/z=534.59 [M]$^+$; Analysis: for C$_{29}$H$_{27}$FN$_2$O$_5$S, calcd. C, 65.15, H, 5.09, N, 5.24, S, 6.00%; found C, 65.30, H, 5.10, N, 5.22, S, 6.01%.

N'-(2,5-dihydroxybenzylidene)-2-((1Z)-1-(4-(methylsulfinyl)benzylidene)-5-fluoro-2-methyl-1H-inden-3-yl)acetohydrazide (21): Yield: 55%; m. p.: 180-182° C.; IR (KBr) cm$^{-1}$: 2915 (NH str.), 1656 (C=O, Str.), 1570 (C=N str.); $^1$H NMR (500 MHz, DMSO-d$_6$): δ=2.21 (3H, s, CH$_3$), 2.81 (3H, s, S=OCH$_3$), 4.01 (2H, s, CH$_2$), 6.71 (1H, s, =CH), 7.17-7.95 (10H, m, Ar—H), 8.38 (1H, s, N=CH), 8.92 (1H, s, OH), 10.21 (1H, s, OH), 11.78 (1H, s, CONH, D$_2$O exchg.); $^{13}$C NMR (125.76 MHz, DMSO-d$_6$): δ=11.0, 29.6, 31.8, 36.2, 106.7, 110.8, 114.0, 117.4, 119.4, 124.4, 129.9, 130.4, 139.0, 140.9, 146.6, 150.3, 162.8, 165.6, 171.0; MS: m/z=490.55 [M]$^+$; Analysis: for C$_{27}$H$_{23}$FN$_2$O$_4$S, calcd. C, 66.11, H, 4.73, N, 5.71, S, 6.54%; found C, 66.30, H, 4.74, N, 5.69, S, 6.55%.

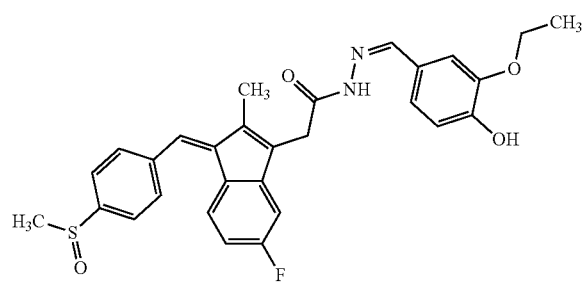

Compound 20

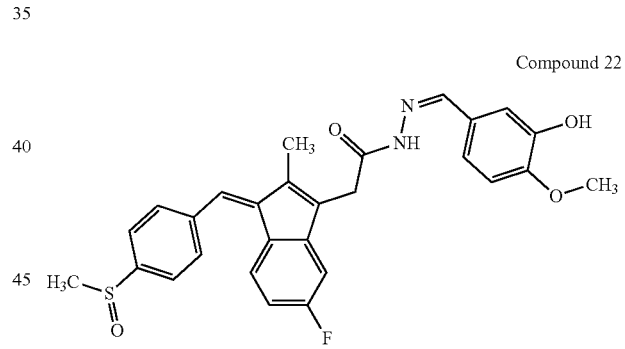

Compound 22

N'-(3-ethoxy-4-hydroxybenzylidene)-2-((1Z)-1-(4-(methylsulfinyl) benzylidene)-5-fluoro-2-methyl-1H-inden-3-yl)acetohydrazide (20). Yield: 60%; m. p.: 193-195° C.; IR (KBr) cm$^{-1}$: 2940 (NH str.), 1661 (C=O, Str.), 1592 (C=N str.); $^1$H NMR (500 MHz, DMSO-d$_6$): δ=1.37 (3H, s, CH$_3$), 2.21 (3H, s, CH$_3$), 2.83 (3H, s, S=OCH$_3$), 3.97 (2H, q, OCH$_2$), 4.04 (2H, s, CH$_2$), 6.83 (1H, s, =CH), 7.15-7.81 (10H, m, Ar—H), 8.16 (1H, s, N=CH), 9.52 (1H, s, OH), 11.31 (1H, s, CONH, D$_2$O exchg.); $^{13}$C NMR (125.76 MHz, DMSO-d$_6$): δ=11.0, 15.2, 30.1, 43.6, 54.3, 110.9, 116.0, 121.9, 123.6, 124.4, 126.0, 129.8, 130.0, 133.8, 138.3, 138.7, 139.1, 140.9, 144.4, 146.5, 147.6, 149.4, 162.3, 163.7, 165.6, 171.2; MS: m/z=520.49 [M+2]$^+$; Analysis: for C$_{29}$H$_{27}$FN$_2$O$_4$S, C 67.16, H, 5.25, N, 5.40, S, 6.18%; found C, 67.35, H 5.24, N, 5.42, S, 6.19%.

N'-(3-hydroxy-4-methoxybenzylidene)-2-((1Z)-1-(4-(methylsulfinyl)benzylidene)-5-fluoro-2-methyl-1H-inden-3-yl)acetohydrazide (22): Yield: 58%; m. p.: 208-210° C.; IR (KBr) cm$^{-1}$: 3023 (NH str.), 1657 (C=O, Str.), 1569 (C=N str.); $^1$H NMR (500 MHz, DMSO-d$_6$): δ=2.22 (3H, s, CH$_3$), 2.82 (3H, s, S=OCH$_3$), 3.56 (1H, s, CH$_2$), 3.80 (3H, s, OCH$_3$), 3.98 (1H, s, CH$_2$), 6.71 (1H, s, =CH), 6.95-7.80 (10H, m, Ar—H), 7.92 (1H, s, N=CH), 9.24 (1H, s, OH), 11.32 (1H, s, CONH, D$_2$O exchg.); $^{13}$C NMR (125.76 MHz, DMSO-d$_6$): δ=10.9, 29.7, 32.0, 43.5, 56.0, 106.7, 112.6, 120.3, 120.7, 127.4, 130.4, 138.4, 138.6, 139.0, 140.8, 144.1, 147.2, 150.2, 162.2, 163.6, 165.5, 171.1; MS: m/z=504.94[M]$^+$; Analysis: for C$_{28}$H$_{25}$FN$_2$O$_4$S, calcd. C, 66.65, H, 4.99, N, 5.55, S, 6.35%; found C, 66.45, H, 4.98, N, 5.56, S, 6.36%.

Compound 23

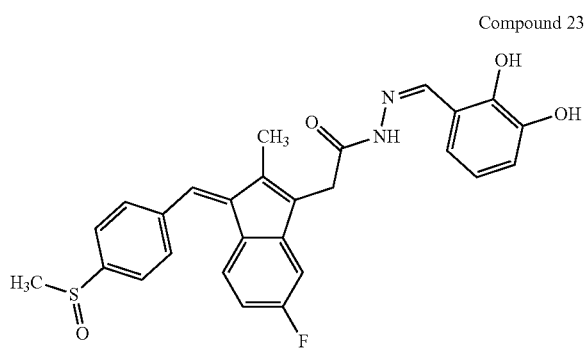 [SMILES: CC1=C(CC(=O)N/N=C\c2cccc(O)c2O)c2cc(F)ccc2/C1=C\c1ccc(S(C)=O)cc1]

N'-(2,3-dihydroxybenzylidene)-2-((1Z)-1-(4-(methylsulfinyl)benzylidene)-5-fluoro-2-methyl-1H-inden-3-yl)acetohydrazide (23): Yield: 52%; m. p.: 220-222° C.; IR (KBr) cm$^{-1}$: 3060 (NH str.), 1671 (C=O, Str.), 1596 (C=N str.); $^1$H NMR (500 MHz, DMSO-d$_6$): δ=2.20 (3H, s, CH$_3$), 2.82 (3H, s, S=OCH$_3$), 3.61 (1H, s, CH$_2$), 3.97 (1H, s, CH$_2$), 6.69 (1H, s, =CH), 6.82-7.91 (10H, m, Ar—H), 8.42 (1H, s, N=CH), 9.11 (1H, s, OH), 9.21 (1H, s, OH), 11.32 (1H, s, CONH, D$_2$O exchg.); $^{13}$C NMR (125.76 MHz, DMSO-d$_6$): δ=10.9, 31.7, 43.5, 110.7, 111.0, 116.9, 117.1, 117.8, 119.1, 119.6, 120.3, 121.2, 124.4, 130.4, 133.1, 133.8, 138.4, 138.9, 139.0, 140.8, 146.0, 146.6, 146.7, 148.3, 165.6, 171.0; MS: m/z=490.70 [M]$^+$; Analysis: for C$_{27}$H$_{23}$FN$_2$O$_4$S, calcd. C, 66.11, H, 4.73, N, 5.71, S, 6.54%; found C, 66.33, H, 5.72, N, 5.68, S, 6.53%.

Compound 24

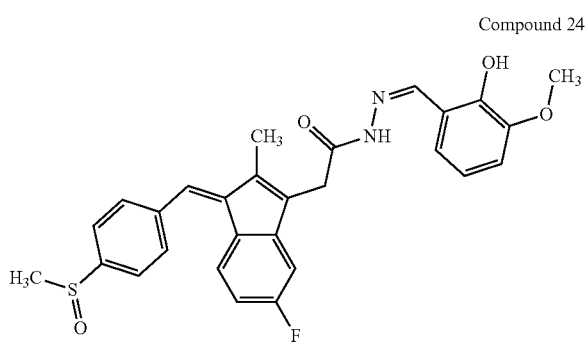

N'-(2-hydroxy-3-methoxymethoxybenzylidene)-2-((1Z)-1-(4-(methylsulfinyl)benzylidene)-5-fluoro-2-methyl-1H-inden-3-yl)acetohydrazide (24): Yield: 55%; m. p.: 210-212° C.; IR (KBr) cm$^{-1}$: 3051 (NH str.), 1693 (C=O, Str.), 1599 (C=N str.); $^1$H NMR (500 MHz, DMSO-d$_6$): δ=2.20 (3H, s, CH$_3$), 2.82 (3H, s, S=OCH$_3$), 3.60 (1H, s, CH$_2$), 3.80 (3H, s, OCH$_3$), 3.97 (1H, s, CH$_2$), 6.71 (1H, s, =CH), 6.80-7.80 (10H, m, Ar—H), 8.48 (1H, s, N=CH), 10.40 (1H, s, OH), 11.45 (1H, s, CONH, D$_2$O exchg.); $^{13}$C NMR (125.76 MHz, DMSO-d$_6$): δ=10.9, 29.9, 31.7, 43.5, 56.2, 106.7, 113.2, 114.1, 118.0, 119.3, 119.4, 119.6, 121.3, 130.4, 138.3, 138.8, 138.9, 139.0, 140.8, 141.0, 147.4, 162.2, 162.3, 163.7, 165.6, 171.2; MS: m/z=504.34 [M]$^+$; Analysis: for C$_{28}$H$_{25}$FN$_2$O$_4$S, calcd. C, 66.65, H, 4.99, N, 5.55, S, 6.35%; found C, 66.85, H, 4.50, N, 5.53, S, 6.34%.

Compound 25

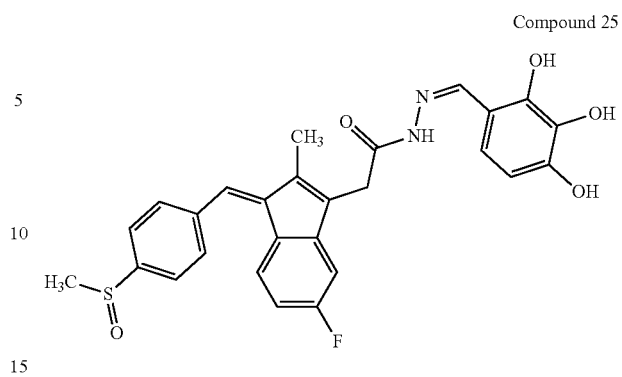

N'-(2,3,4-trihydroxybenzylidene)-2-((1Z)-1-(4-(methylsulfinyl)benzylidene)-5-fluoro-2-methyl-1H-inden-3-yl)acetohydrazide (25): Yield: 50%; m. p.: 195-197° C.; IR (KBr) cm$^{-1}$: 3051 (NH str.), 1668 (C=O, Str.), 1598 (C=N str.); $^1$H NMR (500 MHz, DMSO-d$_6$): δ=2.20 (3H, s, CH$_3$), 2.83 (3H, s, S=OCH$_3$), 3.59 (1H, s, CH$_2$), 6.38 (1H, s, =CH), 6.71-7.80 (10H, m, Ar—H), 8.30 (1H, s, N=CH), 9.24 (1H, s, OH), 11.32 (1H, s, CONH, D$_2$O exchg.); $^{13}$C NMR (125.76 MHz, DMSO-d$_6$): δ=10.9, 29.7, 31.7, 43.5, 108.0, 111.1, 121.5, 124.4, 130.4, 133.1, 138.8, 139.0, 140.8, 146.7, 147.8, 149.2, 149.5, 162.3, 163.7, 165.2, 170.5; MS: m/z=504.94 [M−1]$^+$; Analysis: for C$_{27}$H$_{23}$FN$_2$O$_5$S, calcd. C, 64.02, H, 4.58, N, 5.53, S, 6.33%; found C, 64.19, H, 4.57, N, 5.55, S, 6.31%.

Example 2

Antioxidant Activity of Sulindac Derivatives

The antioxidant activity was measured based on the scavenging activity of the stable DPPH free radical. 100 μg/mL of the twenty-five sulindac derivative compounds were added to 3 mL 0.004% DPPH solution. Methanol was added to 3 mL 0.004% DPPH solution for the control sample. Absorbance was determined at 520 nm after 30 min. Butylated hydroxytoluene (BHT) was used as a reference drug. The percent inhibition was calculated by the equation:

$$A_0 - \frac{A_t}{A_0} \times 100,$$

where $A_t$ is the absorbance of the compound and $A_0$ is the absorbance of the control. The scavenging effects expressed as a percentage±STD are summarized in Table 1.

TABLE 1

| Antioxidant activity of sulindac derivatives | |
|---|---|
| Compound | Scavenging Effect |
| 1 | 18.53 ± 4.86 |
| 2 | 19.26 ± 5.32 |
| 3 | 67.40 ± 9.25 |
| 4 | 39.86 ± 10.80 |
| 5 | 42.20 ± 13.20 |
| 6 | 71.03 ± 5.31 |
| 7 | 49.36 ± 5.57 |
| 8 | 85.10 ± 6.80 |
| 9 | 78.97 ± 9.36 |
| 10 | 42.33 ± 18.38 |
| 11 | 45.06 ± 22.57 |
| 12 | 39.73 ± 15.65 |

TABLE 1-continued

Antioxidant activity of sulindac derivatives

| Compound | Scavenging Effect |
|---|---|
| 13 | 23.07 ± 6.95 |
| 14 | 62.93 ± 6.72 |
| 15 | 40.60 ± 14.40 |
| 16 | 30.80 ± 2.50 |
| 17 | 63.56 ± 0.47 |
| 18 | 37.90 ± 10.35 |
| 18 | 29.66 ± 16.93 |
| 20 | 35.50 ± 9.05 |
| 21 | 38.10 ± 10.92 |
| 22 | 51.40 ± 16.66 |
| 23 | 33.10 ± 8.41 |
| 24 | 27.66 ± 2.12 |
| 25 | 30.06 ± 3.30 |
| BHT | 90.6 ± 3.83 |

Example 3

Animal Tests

All animal experiments used healthy male albino rats (200 g-220 g) and mice. The animals were kept in standard plastic animal cages in groups of six animals each with a 12 hour light and dark cycle. The animals were acclimatized to laboratory conditions for a week prior to the experiments.

In an anti-pyretic study, hyperthermia was induced in mice by subcutaneous injection of 20 mL/kg of a 20% aqueous suspension of brewer's yeast in the back below of nape of the neck. The animals were fasted for 24 hours. Water was made available. Control rectal temperature was recorded 24 hours after the yeast injection to determine the pyretic response to yeast. Rectal temperature recordings were then taken 1 hour prior to drug administration in the fevered animals to serve as a pre drug control. Drugs were administered 24 hours after the yeast injection, and rectal temperatures were recorded at 60, 90 and 120 min. after drug administration. Results were calculated by ANOVA followed by Dunnett's multiple comparison test and are summarized in Table 2.

TABLE 2

Effect of compound 8 and sulindac on yeast-induced hypothermia in mice

| | Compound 8 | Sulindac |
|---|---|---|
| Dose mg/kg | 150 | 100 |
| Normal ° C. | 35.16 ± 0.10 | 35.21 ± 0.11 |
| ° C. Control | 38.38 ± 0.19*** | 38.21 ± 0.31*** |
| ° C. 30 min | 38.15 ± 0.10 | 37.46 ± 0.14 |
| ° C. 60 min | 37.83 ± 0.15* | 37.16 ± 0.09** |
| ° C. 120 min | 37.33 ± 0.12*** | 36.23 ± 0.08*** |

All values represent mean ±SEM; *= $p < 0.05$; = $p < 0.01$; *= $p < 0.001$ (n = 6)

In an analgesic study by tail flick method, acute nociception was assessed using a tail flick apparatus (Tail Flick model DS 20 Sorrel Apelex, France). Briefly, each animal was placed in a restrainer 2 min. before treatment and baseline reaction time was measured by focusing an intensity controlled beam of light on the distal one-third portion of the animal's tail. The suspension was orally administered immediately after this step, and 25 min. later the post drug reaction time was measured. A 10 sec cut off time was used in order to prevent tissue damage. Results were calculated by ANOVA, followed by Dunnett's multiple comparison test, and are summarized in Table 3.

TABLE 3

Analgesic effect by tail flick method in mice

| | Compound 8 | Sulindac |
|---|---|---|
| Dose mg/kg | 150 | 100 |
| | Reaction Time (seconds) | |
| Pre-drug | 5.00 ± 0.36 | 4.83 ± 0.40 |
| 30 min | 4.83 ± 0.30 | 5.50 ± 0.34 |
| % Inhibition | 3.33 | 13.79 |
| 60 min | 7.33 ± 0.42** | 8.83 ± 0.79** |
| % Inhibition | 46.66 | 82.75 |
| 120 min | 7.16 ± 0.30*** | 11.00 ± 0.57*** |
| % Inhibition | 63.33 | 127.58 |

All values represent mean ±SEM; = $p < 0.01$; *= $p < 0.001$ (n = 6)

In an analgesic activity by hot plate method study, animals were dropped gently on a hot plate maintained at 55±5.5° C. Reaction time was recorded as the interval extending from the instant the animal reached the hot plate until the moment the animal licked its forefeet or jumped off. Reaction time was measured 10 min. before the oral administration of test compounds and 60, 90, and 120 min. after administration. Results were calculated by ANOVA followed by Dunnett's multiple comparison test, and are summarized in Table 4.

TABLE 4

Analgesic effect by hot plate method in mice

| | Compound 8 | Sulindac |
|---|---|---|
| Dose mg/kg | 150 | 100 |
| | Reaction Time (seconds) | |
| Pre-drug | 6.66 ± 0.33 | 7.66 ± 0.33 |
| 30 min | 7.66 ± 0.42 | 10.83 ± 0.47*** |
| % Inhibition | 15 | 41.30 |
| 60 min | 9.83 ± 0.30*** | 11.83 ± 0.47*** |
| % Inhibition | 47.50 | 54.34 |
| 120 min | 11.16 ± 0.30*** | 14.33 ± 0.42*** |
| % Inhibition | 67.50 | 86.95 |

All values represent mean ±SEM; ***= $p < 0.001$ (n = 6)

In an analgesic activity by writhing study, writhing was induced in mice by intraperitoneal administration of 0.1 mL of 1% acetic acid. The number of writhing movements was counted for 20 minutes. The writhing test was performed after the administration of the vehicle or sulindac derivative compound. Results were calculated by ANOVA followed by Dunnett's multiple comparison test and are summarized in Table 5.

TABLE 5

Analgesic Effect of Drugs by Acetic Acid Induced Writhing in Mice

| | mg/kg | Movements | % Inhibition |
|---|---|---|---|
| Compound 8 | 150 | 14.66 ± 0.95*** | 56.86 |
| Sulindac | 100 | 8.83 ± 0.70*** | 74.01 |
| Acetic Acid | 0.1 ml of 20% | 34.00 ± 1.23 | — |

All values represent mean ±SEM; ***= $p < 0.001$ (n = 6)

In a Carrageenan induced paw edema in rats study, Carrageenan sodium salt (0.05 mL of 1% BDH) was injected into the right hind foot of each rat (male or female, 200-220 g) under the plantar aponeurosis. The test group of was treated orally with a Sulindac derivative compound 1 hour before carrageenan injection. At the same time, the control group was given 5 mL/kg of normal saline and the reference group was given 100 mg/kg of an aqueous solution of sulindac. Foot volume was measured by the displacement technique using a plethysmometer (Apelex, France) immediately after and 2 and 3 hours after the injection of carrageenan. Inhibitory activity was calculated using the following:

$$100 \times \left(1 - \frac{(A-X)}{(B-Y)}\right),$$

where "B" is the mean paw volume of control rats after carrageenan injection, "Y" is the mean paw volume of control rats before the carrageenan injection, "X" is the mean paw volume of treated rats before carrageenan injection, and "A" is the mean paw volume of treated rats after the carrageenan injection. Results were calculated by ANOVA followed by Dunnett's multiple comparison test and are summarized in Table 6.

TABLE 6

Anti-inflammatory activity by carrageenan-induced paw edema method

|  | Carrageenan only | Compound 8 | Sulindac |
|---|---|---|---|
| Dose (mg/kg) |  | 150 | 100 |
| Before carrageenan | 1.04 ± 0.02 | 1.02 ± 0.02 | 1.03 ± 0.03 |
| Increased paw volume after 3 hours | | | |
| Mean | 1.68 ± 0.01*** | 1.34 ± 0.02*** | 1.26 ± 0.03** |
| Net | 0.63 ± 0.01 | 0.31 ± 0.03*** | 0.22 ± 0.01*** |
| % Inhibition | — | 50.52 | 65.18 |
| Increased paw volume after 5 hours | | | |
| Mean | 1.65 ± 0.01*** | 1.33 ± 0.01*** | 1.25 ± 0.03*** |
| Net | 0.61 ± 0.02 | 0.30 ± 0.02*** | 1.25 ± 0.03*** |
| % Inhibition | — | 50.54 | 65.02 |

All values represent mean ±SEM; = $p < 0.01$; *= $p < 0.001$ (n = 6)

In an ulcer study of sulindac derivatives using 80% ethanol, the ethanol-induced ulcer model was used to study gastro-protective activity of sulindac derivative Compound 8. Rats were grouped into five groups (n=6). Group I received 80% ethanol only and served as an ulcer control. Group II received 80% ethanol and sulindac (100 mg/kg) orally. Group III received 80% ethanol and sulindac derivative Compound 8 (50 mg/kg) orally and served as the experimental treatment group. Animals in Group IV received sulindac (100 mg/kg body weight) without any ethanol. Animals in group V received sulindac derivative Compound 8 (50 mg/kg) without any ethanol. Animals of all Groups were sacrificed 1 hour later under anesthesia and their stomachs were quickly removed for further studies. The stomach was opened along the greater curvature, washed with distilled water and cleaned gently by dipping in saline. The mucosal damage was assessed according to the following scoring system: redness=0.5, spot ulcer=1.0, hemorrhagic streaks=1.5, ulcer>3 but<5=2.0, ulcers>5=3.0. The mean score of each treated group minus the mean score of the control group was taken as the severity index of gastric mucosal damage. Results were calculated by ANOVA followed by Dunnett's multiple comparison test and are summarized in Table 7, represent mean±SEM; ***=$p<0.001$ (n=6).

TABLE 7

Ulcer Study of Sulindac Derivatives

| Treatment | Dose (mg/kg) | Ulcer Index | % Inhibition |
|---|---|---|---|
| 80% EtOH | 1 mL/200 g Rat | 7.33 ± 0.33 | |
| 80% EtOH + sulindac | 100 | 6.83 ± 0.40 | 6.81 |
| 80% EtOH + Cmpd 8 | 150 | 4.33 ± 0.4*** | 40.90 |
| sulindac | 100 | 1.33 ± 0.49 | |
| Compound 8 | 150 | — | |

All values represent mean ±SEM; ***= $p < 0.001$ (n = 6)

In a study of the effect of sulindac derivatives on gastric lesions induced by indomethacin, a suspension of indomethacin in 1.0% carboxymethylcellulose (CMC) in water (6 mg/mL) at a dose of (30 mg/kg) body weight was administered orally to rats. Control rats were treated with the vehicle. Sulindac derivative Compound 8 was administered half an hour prior to indomethacin administration at a dose of 150 mg/kg. Results were calculated by ANOVA followed by Dunnett's multiple comparison test and are summarized in Table 8.

TABLE 8

Ulcer Study of Sulindac Derivative in Rats Given Indomethacin

| Treatment | Dose (mg/kg) | Ulcer Index | % Inhibition |
|---|---|---|---|
| Indomethacin Alone | 30 | 37.00 ± 1.59 | |
| Sulindac | 100 | 32.00 ± 3.86 | |
| Compound 8 | 150 | 22.16 ± 1.10*** | 40.09 |

All values represent mean ±SEM; ***= $p < 0.001$ (n = 6)

In a study for the determination of malondialdehyde, non-protein sulfhydryls, and total protein, stomach tissues were removed from rats, and each tissue was homogenized in 0.15M KCl to give a 10% w/v homogenate. Aliquots of homogenate (1 mL) were incubated at 37° C. for three hours in a metabolic shaker. Then 1 mL of 10% aqueous trichloroacetic acid was added to the homogenate and mixed. This suspension was then centrifuged at 4000 rpm for 10 min. A total of 1 mL of supernatant was removed and mixed with 1 mL of 0.67% thiobarbituric acid in water and placed in a boiling water bath for 10 min. The mixture was cooled and diluted with 1 mL of distilled water. The absorbance of the solution was then read at 535 nm. The content of malondialdehyde (MDA) (nmol/g) was then calculated by reference to a standard curve of MDA solution.

Hepatic non-protein sulfhydryls (NP-SH) were measured by homogenizing rat stomach tissues in ice cold 0.02 mmol/L ethylenediaminetetraacetic acid (EDTA). Aliquots of 5 mL of the homogenates were mixed in 15 mL test tube with 4 mL of distilled water and 1 mL of 50% trichloroacetic acid (TCA). The test tubes were shaken intermittently for 10 min. and centrifuged at 3000 rpm for 10 min. A total of 2 mL supernatant was mixed with 4 mL of 0.4 mmol/L tris buffer (pH 8.9). A total of 0.1 mL of 5,5-dithiobis(2-nitrobenzoic acid) (BTNB) was added, and the sample was shaken. The absorbance was measured within 5 min. of addition of DTNB at 412 nm and compared to a reagent blank.

Total Protein (TP), or dissolved proteins in gastric juice, was estimated through alcohol precipitation. 90% alcohol was added to gastric juice at a 9:1 ratio, and then 0.1 ml of the alcoholic precipitate of gastric juice was dissolved in 1 ml of 0.1 N NaOH, and 0.05 ml of this suspension was placed in a test tube. 4 ml of an alkaline mixture was then added to the test tube and incubated at room temperature for 10 minutes. 0.4 ml of a phenol reagent was then added, and after a further 10 minutes, once color had developed, a reading was taken against a blank containing distilled water at 610 nm on a spectrophotometer. TP content was then calculated from a standard curve prepared with bovine albumin and expressed as g/L of gastric juice. Results were calculated by ANOVA followed by Dunnett's multiple comparison test and are summarized in Table 9, represent mean±SEM; =p<0.01; *=p<0.001 (n=6).

TABLE 9

Anti-Oxidant Activity, MDA, NP-SH, and Total Protein

| Treatment | Dose (mg/dL) | MDA (nmol/g) | NP-SH (nmol/g) | TP (g/L) |
|---|---|---|---|---|
| Saline | 1 mL | 1.03 ± 0.02 | 8.29 ± 0.53 | 113.37 ± 2.94 |
| 80% Ethanol | 1 mL | 6.53 ± 0.56*** | 3.04 ± 0.39*** | 47.90 ± 2.89*** |
| 80% Ethanol + Sulindac | 1 mL + 100 | 2.28 ± 0.11*** | 5.08 ± 0.28** | 93.81 ± 3.05*** |
| 80% Ethanol + Compound 8 | mL + 150 | 1.59 ± 0.06*** | 6.62 ± 0.26*** | 100.99 ± 2.42*** |
| Sulindac | 100 | 1.31 ± 0.04*** | 7.00 ± 0.032*** | 105.78 ± 1.43*** |
| Compound 8 | 150 | 1.06 ± 0.02*** | 7.52 ± 0.31*** | 114.57 ± 1.89*** |

In a study of the $LD_{50}$ of sulindac derivative Compound 8, the $LD_{50}$ (lethal dose 50%) was calculated for compound 8 by the Karber method. For determination of $LD_{50}$, an observation was made for 24 hours, and symptoms of toxicity and rate of mortality were noted. Expired animals were counted at the end of the study period for the calculation of $LD_{50}$ according to:

$$LD_{50} = LD_{100} - \Sigma(a \times b)/n,$$

where n is the total number of animals in a group, a is the difference between two successive doses of administered extract/substance, b is the average number of dead animals in two successive doses, and $LD_{100}$ is the lethal dose causing 100% death of all test animals. Results are summarized in Table 10.

TABLE 10

$LD_{50}$ of Sulindac Derivative Compound 8

| Group | Dose (mg/kg) | Dose Increment (a) | # Dead | Mean Mortality (b) | Product (a × b) |
|---|---|---|---|---|---|
| 1 | 100 | | 0 | | |
| 2 | 200 | 100 | 0 | | |
| 3 | 400 | 200 | 1 | 0.5 | 100 |
| 4 | 800 | 400 | 3 | 2 | 800 |
| 5 | 1600 | 800 | 5 | 4 | 3200 |
| 6 | 2000 | 400 | 9 | 7 | 2800 |
| Sum | | | | | 6900 |
| | | | | | 1310 |

It is to be understood that the Sulindac derivatives are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A sulindac derivative, comprising a compound having the formula:

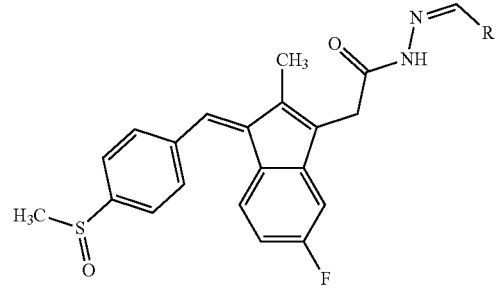

wherein R is selected from the group consisting of 2-nitrophenyl; 4-nitrophenyl; phenyl; 4-chlorophenyl; 3-hydroxyphenyl; 3-methoxyphenyl; 3-nitrophenyl; 4-dimethylaminophenyl; 2,4,5-trimethoxyphenyl; 3,4,5-trimethoxyphenyl; 4-hydroxyphenyl; 2-methoxyphenyl; 2,4-dimethoxyphenyl; 2,3-dimethoxyphenyl; 3,4-dimethoxyphenyl; 2,4,6-trimethoxyphenyl; 2,3,4-trimethoxyphenyl; 3-methoxy-4-ethoxyphenyl; 3,5-dimethoxy-4-hydroxyphenyl; 3-ethoxy-4-hydroxyphenyl; 2,5-dihydroxyphenyl; 3-hydroxy-4-methoxyphenyl; 2,3-dihydroxyphenyl; 2-hydroxy-3-methoxyphenyl; and 2,3,4-trihydroxyphenyl;

or a pharmaceutically acceptable salt thereof.

2. The sulindac derivative of claim 1, wherein R is 4-dimethylaminophenyl.

3. A pharmaceutical composition comprising a sulindac derivative according to claim 1 and a pharmaceutically acceptable carrier.

4. A method of making sulindac derivatives, comprising the steps of:

refluxing a methyl ester of sulindac and hydrazine hydrate in the presence of absolute ethanol to yield 2-[(1 Z)-5-fluoro-1-{[4-(methanesulfinyl) phenyl]methylidene}-2-methyl-1H-inden-3-yl]acetohydrazide; and refluxing a solution including the 2-[(1 Z)-5-fluoro-1-{[4-(methanesulfinyl) phenyl]methylidene}-2-methyl-1H-inden-3-yl]acetohydrazide and a substituted benzaldehyde in the presence of ethanol and glacial acetic acid to yield a 2-(5-methoxy-2-methyl-1-indol-3yl)-N-[(E)-substituted phenyl methylidine] acetohydrazide derivative, having the structure:

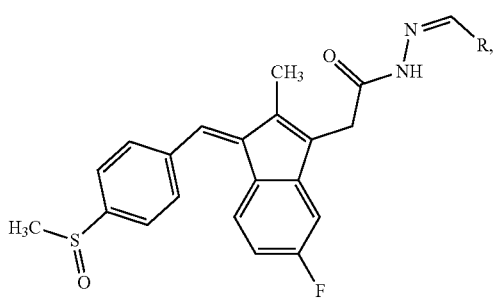

wherein R is selected from the group consisting of 2-nitrophenyl; 4-nitrophenyl; phenyl; 4-chlorophenyl; 3-hydroxyphenyl; 3-methoxyphenyl; 3-nitrophenyl; 4-dimethylaminophenyl; 2,4,5-trimethoxyphenyl; 3,4,5-trimethoxyphenyl; 4-hydroxyphenyl; 2-methoxyphenyl; 2,4-dimethoxyphenyl; 2,3-dimethoxyphenyl; 3,4-dimethoxyphenyl; 2,4,6-trimethoxyphenyl; 2,3,4-trimethoxyphenyl; 3-methoxy-4-ethoxyphenyl; 3,5-dimethoxy-4-hydroxyphenyl; 3-ethoxy-4-hydroxyphenyl; 2,5-dihydroxyphenyl; 3-hydroxy-4-methoxyphenyl; 2,3-dihydroxyphenyl; 2-hydroxy-3-methoxyphenyl; and 2,3,4-trihydroxyphenyl.

5. The method of making sulindac derivatives according to claim 4, wherein the step of refluxing a methyl ester of sulindac and hydrazine hydrate further comprises refluxing the methyl ester of sulindac and hydrazine hydrate in the presence of the absolute ethanol for 30 hours.

6. The method of making sulindac derivatives according to claim 4, wherein the step of refluxing the solution including the 2-[(1Z)-5-fluoro-1-{4-(methanesulfinyl) phenyl]methylidene}-2-methyl-1H-inden-3-yl]acetohydrazide and a substituted benzaldehyde further comprises refluxing the 2-[(1 Z)-5-fluoro-1-{[4-(methanesulfinyl) phenyl]methylidene}-2-methyl-1H-inden-3-yl]acetohydrazide and the substituted benzaldehyde under heat for 3 hours.

7. The method of making sulindac derivatives according to claim 4, further comprising the step of recrystallizing the 2-(5-methoxy-2-methyl-1-indol-3 yl)-N-[(E)-substituted phenyl methylidine] acetohydrazide derivative from ethanol.

* * * * *